(12) United States Patent
Chapples et al.

(10) Patent No.: US 7,794,575 B2
(45) Date of Patent: Sep. 14, 2010

(54) MONITORING OF GAS SENSORS

(75) Inventors: John Chapples, Farlington (GB); Martin Legg, Gussage St. Michael (GB); Neils Hansen, Oakdale (GB)

(73) Assignee: Honeywell Analytics Limited, Poole, Dorset (GB)

( * ) Notice: Subject to any disclaimer, the term of this patent is extended or adjusted under 35 U.S.C. 154(b) by 1179 days.

(21) Appl. No.: 10/481,937

(22) PCT Filed: Jun. 26, 2002

(86) PCT No.: PCT/GB02/02937

§ 371 (c)(1),
(2), (4) Date: Aug. 11, 2004

(87) PCT Pub. No.: WO03/001191

PCT Pub. Date: Jan. 3, 2003

(65) Prior Publication Data

US 2004/0251144 A1    Dec. 16, 2004

(30) Foreign Application Priority Data

Jun. 26, 2001 (GB) ................................. 0115585.2

(51) Int. Cl.
*G01N 27/26* (2006.01)
(52) U.S. Cl. ...................... 204/402; 204/406; 204/431; 205/782
(58) Field of Classification Search ......... 204/400–432; 205/775, 782–786
See application file for complete search history.

(56) References Cited

U.S. PATENT DOCUMENTS 4,123,700 A * 10/1978 LaConti et al. ............. 324/425
4,136,000 A * 1/1979 Davis et al. ................. 204/427
4,366,039 A * 12/1982 Uchida et al. ............... 204/406

(Continued)

FOREIGN PATENT DOCUMENTS

EP    0 840 112    5/1998

(Continued)

OTHER PUBLICATIONS

Robert E. Simpson, Introductory Electronics for Scientists and Engineers, 1987, Allyn and Bacon, Inc., Second Edition, pp. 258-259.*

*Primary Examiner*—Nam X Nguyen
*Assistant Examiner*—Bach T Dinh
(74) *Attorney, Agent, or Firm*—Husch Blackwell Sanders Welsh & Katz

(57) ABSTRACT

A monitor is disclosed for monitoring an atmosphere for the presence of a target gas. The monitor includes an electrical gas sensor having a working (sensing) electrode and a counter electrode, an operational amplifier connected between the sensor electrodes, a detector, and a circuit. The sensor provides a current between the electrodes that is indicative of the amount of a target gas in the atmosphere. The operational amplifier generates an output signal according to the current flowing between the terminals where the output signal is indicative of the amount of target gas in the atmosphere. The detector detects when the current flowing between the sensor electrodes exceeds a predetermined threshold. The circuit restricts the potential difference between the sensor electrodes when the current between the terminals exceeds the predetermined threshold by supplying additional current or removing current from the working sensor electrode.

19 Claims, 3 Drawing Sheets

U.S. PATENT DOCUMENTS

| | | | |
|---|---|---|---|
| 4,664,773 A | * 5/1987 | Suzuki et al. | 204/406 |
| 4,776,203 A | 10/1988 | Jones et al. | |
| 4,965,048 A | * 10/1990 | Ogasawara | 422/54 |
| 5,202,637 A | 4/1993 | Jones | |
| 5,338,431 A | * 8/1994 | Yorita et al. | 204/424 |
| 5,780,715 A | 7/1998 | Imblum | |
| 5,810,997 A | * 9/1998 | Okazaki et al. | 205/784.5 |
| 5,902,467 A | * 5/1999 | Wang et al. | 204/415 |
| 5,935,400 A | * 8/1999 | Takami et al. | 204/425 |
| 6,096,186 A | * 8/2000 | Warburton | 205/782 |
| 6,321,101 B1 | * 11/2001 | Holmstrom | 600/345 |
| 6,758,962 B1 | * 7/2004 | Fitzgerald et al. | 205/783 |

FOREIGN PATENT DOCUMENTS

| | | |
|---|---|---|
| EP | 0 901 014 | 3/1999 |
| JP | 3215737 | 1/1990 |
| WO | 01/31326 | 5/2001 |

* cited by examiner

MONITORING OF GAS SENSORS

CROSS REFERENCE TO RELATED APPLICATION

The present application is the U.S. national stage application of International Application PCT/GB02/02937, filed Jun. 26, 2002, which international application was published on Jan. 3, 2003 as International Publication WO 03/001191. The International Application claims priority of Great Britain Patent Application 0115585.2, filed Jun. 26, 2001.

TECHNICAL FIELD

The present invention relates to the monitoring of sensors that are used for detecting and measuring quantities of gases or vapours in an ambient atmosphere. The present specification will refer to such sensors as "gas sensors", although throughout the present specification that term also applies to the measurement of vapours. The present invention is especially concerned with the monitoring of electrochemical gas sensors, e.g. for measuring toxic gases such as carbon monoxide.

STATE OF THE ART

One use of gas sensors is to monitor the level of carbon monoxide in a dwelling, particularly in temporary accommodation. Various national and international standards apply to the detection of carbon monoxide in dwellings, including a requirement to measure with reasonable accurately up to 600 parts per million (ppm) of carbon monoxide.

After exposure to a large concentration of gas, the reading tends not to return to zero when the toxic gas is no longer present in the atmosphere. Instead, at zero gas, there is a negative reading and the sensor only returns to accurate operation after a substantial recovery time, which can be of the order of days. It would be desirable to reduce the recovery time. In addition, standards are set governing recovery time. For example, CENELEC EN 50192 requires domestic carbon monoxide sensors to respond to carbon monoxide levels up to 50 ppm within one hour of being exposed to a carbon monoxide concentration of 5,000 ppm.

Commercial pressures require such carbon monoxide sensors to be relatively inexpensive; electrochemical sensors include electrodes carrying expensive catalyst, which is usually a metal from the platinum group (Group VIII metal). One way of reducing the cost of such sensors is to restrict the amount of such catalyst used. If a relatively small amount of catalyst is used, the speed of recovery of a sensor from an exposure to a large gas concentration is slow.

The standards applying to carbon monoxide sensing equipment (called herein "monitors") also requires an alarm signal to be generated if the sensor is faulty, for example if the sensor is not properly connected to the electronic circuitry within the monitor or if the sensor has dried out (i.e. lost sufficient volume of electrolyte) or if there is a short circuit between the terminals of the sensor.

It is known to test the viability of an electrochemical gas sensor by imposing an electric pulse across it; U.S. Pat. No. 5,202,637 discloses a three electrode sensor that can be monitored by applying a pulse of potential between the reference electrode and the sensing electrode (also known as the working electrode). Although current does not flow at a significant level between the electrodes, the pulse charges up the double ionic layer at the sensing electrode and this results in a current flow in external circuitry, which can be detected to show that the sensor is operational. Obviously, if the sensor has dried out or if there is a poor connection between the sensor and the circuit, no current will flow and an "error" signal can be generated.

Unfortunately, it is not always possible to detect the pulse when there is a large concentration of gas in the atmosphere being monitored since it can be swamped by the signal from the gas.

In EP-0840112, a sensor is connected to the inverting terminal of an operational amplifier while a voltage pulse is applied periodically to the non-inverting terminal of the amplifier. In normal operation the operational amplifier is acting as a transimpedance amplifier, the gain of which is defined by $V_{out}/I_{input}$ and given by the value of the feedback resistor between the negative input and output of the operational amplifier. If the sensor should become short circuited, the operational amplifier will become a high gain voltage amplifier whose output is the product of the open loop gain and the input offset voltages of the inputs of the operational amplifier. Within low cost operational amplifiers used in domestic types of gas monitors, these parameters can be poorly controlled and as a result the output can be any value including an apparently valid gas reading or an over-range condition. Accordingly, when a pulse is applied to the non-inverting terminal, the amplifier it is not able to determine if the sensor is exposed to an over range high gas concentration or if the sensor has become short circuited.

DISCLOSURE OF INVENTION

According to the present invention, there is provided a monitor for monitoring an atmosphere for the presence of a target gas, the monitor comprising:

a) two terminals for connection, respectively, to the working (sensing) electrode and the counter electrode of an electrochemical gas sensor, the sensor providing a current between the terminals that is indicative of the amount of target gas in the atmosphere;

b) an operational amplifier connected between the sensor electrode terminals to generate an output signal according to the current flowing between the terminals, whereby the output signal is indicative of the amount of target gas in the atmosphere, c) a detector for detecting when the current flowing between the sensor terminals exceeds a predetermined threshold; and d) a circuit that restricts the potential difference between the sensor electrode terminals when the current between the terminals exceeds the predetermined threshold by supplying additional current to or removing additional current from the working sensor terminal.

The detector may detect when the current flowing between the sensor terminals exceeds a predetermined threshold directly or indirectly, for example by monitoring the output signal of the operational amplifier and generating a signal when the amplifier output signal exceeds a threshold value (e.g. when the amplifier output signal is saturated).

The circuit that adjusts the current at the working sensor terminal when the current between the terminals exceeds a predetermined threshold may be an active component such as a transistor between the terminals of the sensor, the circuit reducing the resistance of the transistor when the detector detects an excessive current, thereby allowing current to flow between the sensor terminals. Alternatively, the current may comprise a current source (if the working electrode is an anode) or a current drain (if the working electrode is a cathode) and an active component such as a transistor, e.g. a FET, to connect the current source to the working electrode, thereby reducing the potential difference across the sensor terminals.

The present invention also provides a method of monitoring an atmosphere for the presence of a target gas using the monitor as described above.

DESCRIPTION OF DRAWINGS

The present invention will now be described, by way of example only, with reference to the accompanying drawings in which.

BEST METHOD FOR CARRYING OUT THE INVENTION

Figure 1:
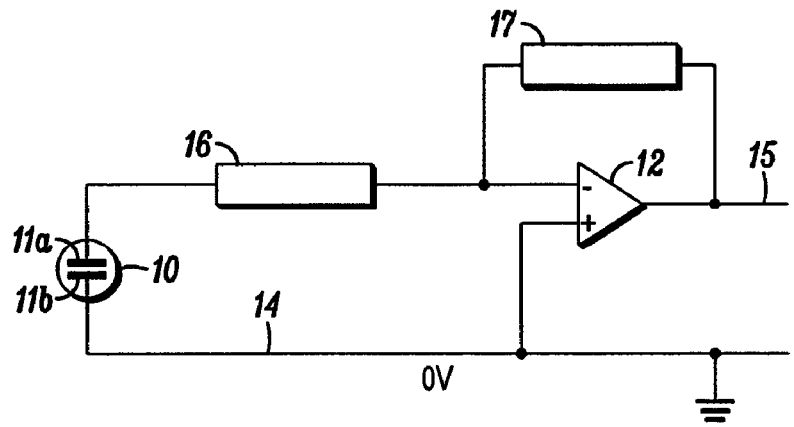
FIG. 1 is a schematic circuit diagram showing a prior art circuit.

Referring initially to FIG. 1, there is shown a known gas monitoring circuit having a two-electrode gas sensor 10, the structure of which is well known (see EP-0,840,112). Essentially, the sensor includes a sensing electrode 11a and a counter electrode 11b separated by an intervening body of electrolyte. The sensing electrode 11a is exposed to the atmosphere being monitored and accordingly any toxic gas (in this carbon monoxide) in the atmosphere comes into contact with the sensing electrode 11a. The sensing electrode 11a is an anode and oxidises the carbon monoxide to carbon dioxide. This oxidation causes a current to flow through the sensor between the working electrode 11a and the counter 11b. A resistor 16 is connected between the sensing electrode 11a and the inverting input of an operational amplifier 12. The non-inverting input of the amplifier is connected to the earth 14. The amplifier has a negative feedback including a resistor 17. The transimpedance gain on the operational amplifier 12 is about 125,000 fold.

The presence of carbon monoxide at the sensing electrode 11a causes the sensing electrode to generate a current proportional to the amount of gas present. The potential difference between the electrodes floats until it reaches a level that is sufficient to generate the current concerned. The current generated at the sensing electrode causes a potential difference across the resistor 16, causing a change of potential at the inverting input of the amplifier 12. The operational amplifier 12 generates a signal at its output that is proportional to the potential between its inputs and so the output signal is proportional to the current flowing in the sensor 10 and hence the amount of gas in the atmosphere being monitored. The output signal can be fed to a display and an alarm (neither shown) to display the concentration of carbon monoxide in the atmosphere and to generate an alarm if the concentration exceeds a pre-set threshold. Alternatively, the integrated concentration can be computed over different time periods to generate alarms based on the rate that the human body absorbs a particular concentration of gas.

By providing a negative feedback, the amplifier attempts to maintain a fixed offset potential (usually zero) between its inputs. The size of the feedback current is proportional to the output signal. In these circumstances, the potential difference between the sensing and reference electrodes fluctuates within a relatively narrow range.

Figure 2:
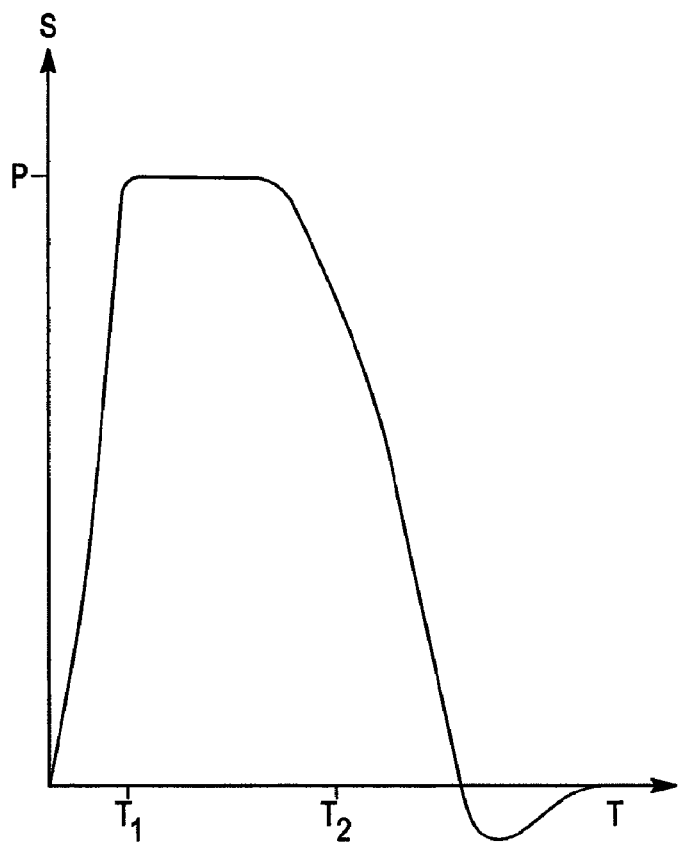
FIG. 2 is a graph showing the output of a gas monitor over time when exposed to a high concentration of carbon monoxide.

FIG. 2 is a graph showing the signal at the amplifier output 15 against time when the sensor is exposed to a substantial level of carbon monoxide in the atmosphere being monitored. The signal rises rapidly until time $t_1$ where the signal is saturated as it reaches a plateau P. At time $t_2$ the carbon monoxide is removed from the atmosphere surrounding the sensor and the current falls. However, it does not fall to a zero signal but overshoots. If the operational amplifier is operated from a split supply rail the output would go negative for a period until it recovers. However, these circuits are typically run from a single supply and so the output would be zero, even in the presence of a certain amount of carbon monoxide. The "negative" signal is probably due to the chemistry in the cell altering when the potential between the electrodes is high.

It can take some considerable time for the signal to return to a zero value when in contact with an atmosphere free of carbon monoxide. CENELEC require a cell to recover within one hour after exposure to 5000 ppm carbon monoxide. This may be difficult to achieve when the sensing and counter electrodes contain a relatively small amount of catalyst, which is desirable commercially in order to reduce its cost.

We have discovered that if the load across the sensor 10 is reduced when passing high currents, particularly when the operational amplifier is saturated, the sensor will recover more quickly. By "load", we mean the requirement on the cell to increase the potential between its electrodes when exposed to more target gas in the atmosphere being monitored in order to pass more current. If the working electrode is an anode, this reduction in load can be achieved by injecting additional current to the working electrode which, together with the current from the amplifier feedback circuit, provides the current that the cell requires to oxidise all the target gas it is in contact with. If the working electrode is a cathode, excessive current may be drained from the working electrode if the amplifier feedback circuit cannot drain all the current generated by the working cathode.

In this specification, the term "current" is used in the conventional electrical sense, i.e. current flows in the opposite direction to the electron flow.

Figure 3:
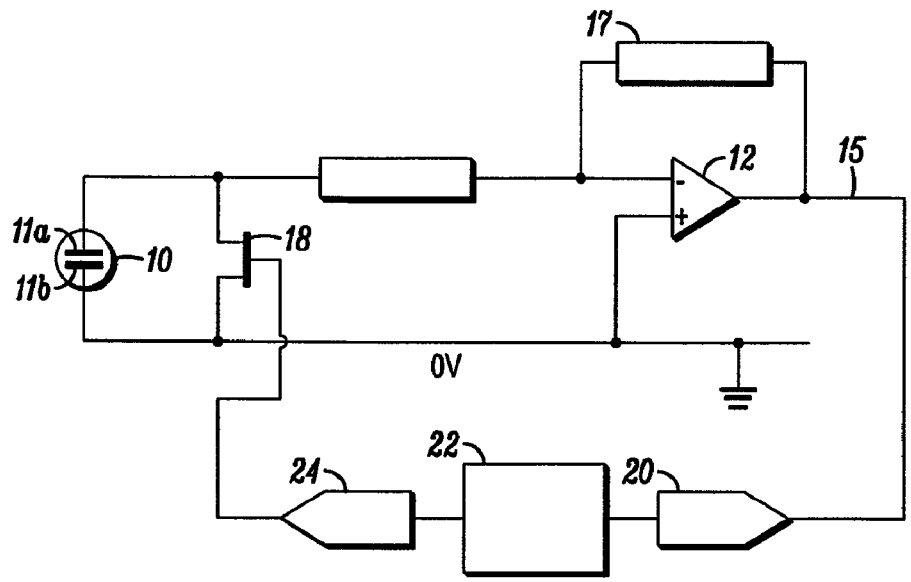
FIG. 3 is a schematic circuit diagram showing the operation of the present invention.

The variation in the load can be achieved in several ways. FIG. 3 shows one method of varying the load; components illustrated in FIG. 3 that are identical to those illustrated in FIG. 1 are indicated by the same reference number.

In FIG. 3, a field effect transistor (FET) 18 is included between the working and counter electrodes of the sensor 10. It usually has a very high resistance between its drain and source so that little or no current flows through it and the circuit operates in the same way as described in connection with FIG. 1. The amplifier output 15 is connected via an analogue-to-digital converter 20 to a microprocessor 22, which monitors the output signal on output 15. If the output signal is saturated, i.e. reaches a threshold level, the current supplied by the feedback resistor is limited; in these circumstances, the microprocessor 22 generates a signal to a digital-to-analogue converter 24 which reduces the resistance of the FET 18. This allows a current to flow from the counter electrode 11b to the working electrode 11a which, together with the current supplied through the feedback resistor 17, supplies the full current required by the working electrode to oxidise all the carbon monoxide molecules that diffuse into contact with the working electrode, The addition of additional current prevents the potential between the electrodes in the sensor 10 from increasing markedly in order to pass the current required by the concentration of CO in contact with the working electrode 11a.

The microprocessor 22 continues reducing the resistance of the FET 18 until the output signal of the amplifier is no longer saturated. Once that state of affairs has been reached, the microprocessor 22 periodically increases the resistance of the FET 18 until the output is again saturated, whereupon it promptly reduces the resistance again to achieve an output signal just below the saturation level. If the concentration of CO in the atmosphere reduces, the microprocessor will return the circuit to its usual operational state, in which the resistance of FET 18 is high, automatically using the above operating regime.

While the resistance of the FET 18 is in a reduced state, the output signal of the amplifier 12 will not give a measure of the amount of gas in the atmosphere. The reduction in the resistance 18 across the sensor 10 can be measured and used to give an indication of the amount of gas in the atmosphere being monitored, as follows. The microprocessor 22 will control the resistance of FET 18 to an extent to bring the output signal 15 down to a predetermined level just below saturation. The amount of gas needed to cause the signal output 15 to be saturated is known. The reduction of resistance of FET 18 can be correlated with the amount of gas in the atmosphere. Accordingly, the reduction in the resistance gives an indication of the amount of gas in the atmosphere over and above the amount of gas required to maintain a signal at the saturated level. Although this generally will not be a particularly accurate measure, nevertheless, it is useful. The resistance reduction can be calculated, for example, by the microprocessor 22.

A circuit (not shown) is known that applies a pulse of potential across the sensor to monitor the viability of the sensor. If the sensor is viable, a pulse in the output circuit is produced that can be detected. However the output pulse will be difficult to detect if the amplifier output is saturated By reducing the amplifier output to below saturation, in accordance with the present invention, it will still be possible to monitor the sensor since the output will no longer be saturated at high gas concentrations and so the pulse in the output signal as a result of the pulse of potential applied between the electrodes of the sensor can still be detected.

Finally, the output signal will take a shorter time to recover after an exposure to a high gas concentration. Typically the output of the sensor to 50 ppm gas would be reduced to only 40 to 50% of its normal reading following an exposure to 5000 ppm for 15 minute followed by 60 minutes in clean air. With this technique the output response to 50 ppm following the same process would typically be 85 to 95% of normal.

Instead of responding to a saturated amplifier output signal, the microprocessor 22 can be set to respond to a lower signal, i.e. when the signal is at a threshold below saturation.

Figure 4:
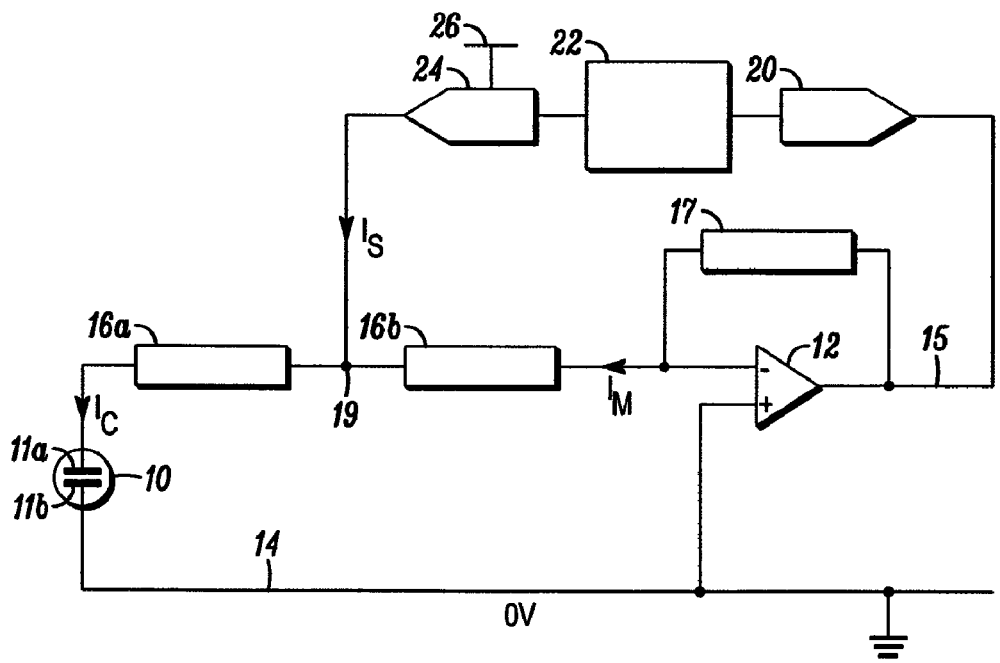
FIG. 4 is a further schematic circuit diagram showing a circuit of the present invention.

An alternative circuit is shown in FIG. 4 (again the components already described will be indicated with the same reference numbers). The FIG. 4 circuit differs from the FIG. 3 circuit in that no FET 18 is provided and instead, the digital-to-analogue converter 24 is connected to the monitor power supply, e.g. a battery (not shown), via a power supply rail 26. Also, the resistor 16 in FIG. 3 is split into two separate resistors 16a and 16b.

In the FIG. 4 circuit, if the microprocessor 22 detects that the output of the amplifier is saturated, the digital-to-analogue converter 24 injects current from the power rail 26 into the sensor circuit at point 19 between the two resistors 16a and 16b. The injected current $I_s$, together with the current $I_m$ supplied through the feedback resistor 17, supplies the full current $I_c$ required by the working electrode 11a to oxidise all the carbon monoxide molecules that diffuse into contact with the working electrode. Once the amplifier output 15 is saturated, the microprocessor 22 increases the amount of current injected from rail 26 until the output signal of the amplifier is no longer saturated. Once that has been achieved, the microprocessor 22 periodically decreases the injected current until the output is again saturated, whereupon it increases the current again to achieve an amplifier output signal below the saturation level. If the concentration of CO in the atmosphere reduces, the microprocessor 22 will return the circuit to its usual operational state (with no current being injected) automatically using the above operating regime.

The circuit of FIG. 4 has the same advantages as described above in connection with FIG. 3.

A working circuit corresponding to the schematic circuit of FIG. 4 will now be described in connection with FIG. 5. The components shown in both FIGS. 4 and 5 are indicated by the same reference numbers.

The microprocessor 22 includes a square wave generator 22' (PWM Output) that is connected to the base of a transistor Q1 that is connected also to the supply rail 26 of the monitor. Resistor R1 and capacitor C3 provide a low frequency filter that filters out the frequency of the square wave and so a voltage is applied to the base of the transistor that is the weighted average of the peaks and troughs of the applied square wave, i.e. if the peaks and troughs are of equal duration, the voltage applied to the gate will be half that voltage of the peak voltage and if the peaks are of much longer than the troughs, the voltage supplied to the base is a little less than the voltage of the supply. The transistor Q1 acts as an emitter follower so that the voltage of the emitter is 0.7 volts less than that applied to the gate of Q1. In this way, the voltage applied by the transistor Q1 to a diode D3 can be set by altering the ratio of the durations of the peaks and troughs from the square wave generator 22'. The emitter of transistor Q1 is connected via diode D3 and a resistor R3 to a point 33 and so the current supplied to the point 33 from the transistor Q1 can be controlled by adjusting the ratio of the peaks of the square wave from generator 22' to the troughs.

Section 32 of the circuit is a charge pump providing a constant voltage of −3 volts at point 31 of the circuit. Section 34 containing transistors Q2 and Q3 is a constant current source providing a current of −30 µA to point 33 at the voltage of point 31, i.e. −3V, irrespective of the peaks and troughs of the square wave generator 22. By controlling the square wave generator to produce no peaks for a short period, no current is applied to point 33 by transistor Q1 and so the current flowing at point 33 and hence at point 19 will be −30 µA. By controlling the square wave generator to provide an appropriate proportion of peaks, the transistor Q1 can be made to supply a current of +60 µA at point 33, which results in a current of +30 µA being supplied to the point 19. In this way, successive positive and negative pulses of 30 µA and −30 µA can be applied to point 19. If the square wave contains an appropriate proportion of peaks, the transistor Q1 can be made to supply a current of +30 µA at point 33, which cancels the current from sections 32 and 34 and hence no current flows to point 19. If a current of, for example +330 µA, is supplied by the transistor Q1 under the control of the square wave generator 22', then a current of +300 µA is supplied to the point 19. In this way, the current supplied to point 19 can be controlled and the circuit will operate as already described in connection with FIG. 4.

Figure 5:
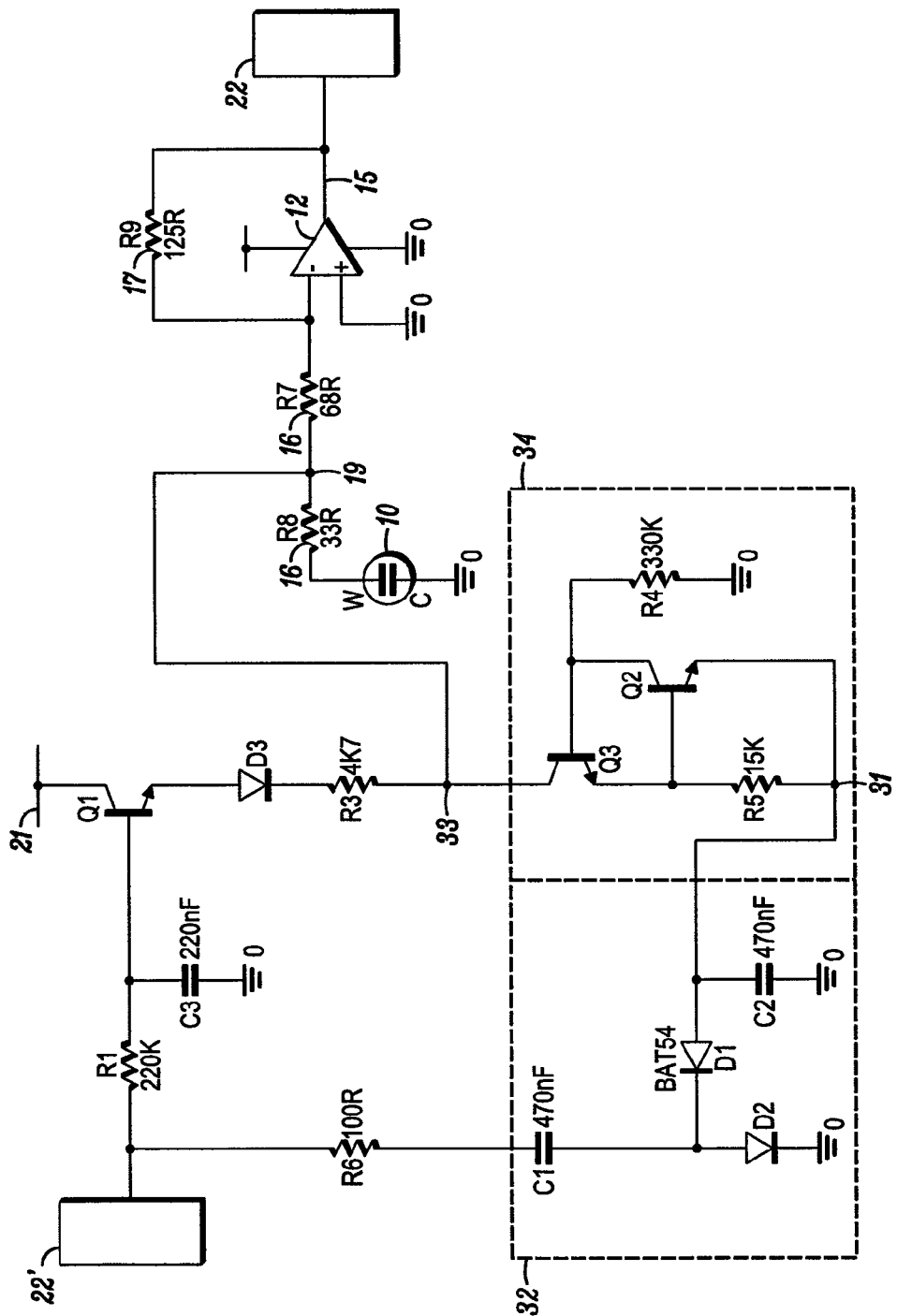
FIG. 5 is a detailed circuit diagram of the circuit of FIG. 4.

The circuit of FIG. 5 can be used to apply pulses periodically to the sensor to detect whether it is viable. This is achieved by the transistor Q1, under the control of the microprocessor 22, supplying virtually no current to point 33 causing a pulse of −30 µA to be applied to point 19 by the charge pump and constant current source 32,34. After about 600 milliseconds a current of +60 μA is supplied by transistor Q1 to point 33 causing a pulse of +30 μA to be applied to point 19. After a further 600 milliseconds, the output of the transistor Q1 returns to the normal state of affairs described above. The double pulses can be applied periodically, e.g. every minute, to ensure that the sensor is functioning properly. The proper functioning of the sensor is detected by a change in the signal over the course of a pulse caused by the current pulses charging or discharging the charge on the working electrode. If the working electrode is not functioning properly or the sensor is not connected properly (or at all) or if there is a short circuit across the sensor, the signal will not change so much (or at all) over the course of the pulse and so this is indicative of a fault in the monitor's functioning.

In the case of a CO sensor 10, the normal state of affairs will be for the square wave generator to be dormant, i.e. it does not generate any square waves. This removes the power supply to transistor Q1 and the charge pump 32 and hence no current will be supplied at point 19. If however, a saturated signal is generated by amplifier 12, this will be detected by the microprocessor 22 and the square wave generator will be reactivated and, under the control of the wave generator 22', an appropriate current can be injected at point 19 to bring the output signal below the saturation level.

As already discussed, there is a tendency for the output of the sensor to produce a current in the opposite direction from that normally produced (i.e. when there is target gas in the atmosphere being monitored) following exposure to high gas concentrations and subsequent removal of the gas, i.e. conventional current flows out of the working anode electrode. By injecting short pulses of −30 μA into the cell to oppose this current, the time for the sensor cell to recover normal operation is decreased. Thus if the output of the sensor cell is negative, which in a single rail monitor means that the output of the operational amplifier is zero, such short pulses of current will assist in bringing the sensor back to its normal operational state more quickly.

The circuit of FIG. 5 can also be used to detect a short circuit in a different way. As stated above, the signal produced when the sensor is short circuited can be any value, depending on the offset voltage of the operational amplifier 12. Usually, however, the output signal of the operational amplifier will be saturated and hitherto it has been impossible to tell that condition from the condition in which there is an excessive amount of gas in the atmosphere. However, if there is an excessive amount of gas in the atmosphere, the circuit of FIG. 5 will be able to bring the amplifier output down to a level in which it is not longer saturated, as described above, but if there is a short circuit, it will not be able to and so a signal indicating that there is a short circuit can be generated in these circumstances.

In practice, the ADC 20, the microprocessor 22 (including the square wave generator 22') and the DAC 24 are all part of one microprocessor chip.

The invention claimed is:

1. A monitor for use with a 2-terminal sensor for monitoring an atmosphere for the presence of a target gas, the monitor comprising:
   a) two terminals for connection, respectively, to a working (sensing) electrode and a counter electrode of an electrochemical gas sensor, the sensor providing a current between the terminals that is indicative of the amount of target gas in the atmosphere, said monitor having only two contacts for connection to a 2-terminal sensor;
   b) an inverting operational amplifier, an inverting input of the inverting operational amplifier coupled to the working (sensing) electrode of the electrochemical gas sensor via a first pathway and a non-inverting input of the inverting operational amplifier coupled to ground to generate an output signal according to the current flowing between the terminals, whereby the output signal is indicative of the amount of target gas in the atmosphere,
   c) a detector for detecting when the current flowing between the sensor terminals exceeds a predetermined threshold associated with saturation of the inverting operational amplifier; and
   d) a circuit that restricts the potential difference between the sensor electrode terminals by detecting that the current between the terminals exceeds the predetermined threshold and by injecting additional current to or removing current from the working sensor terminal via the first pathway in order to oxidize substantially all of the target gas in contact with the working electrode until the inverting operational amplifier is no longer saturated.

2. A monitor as claimed in claim 1, wherein the detector detects when the current flowing between the sensor terminals exceeds a predetermined threshold by monitoring the output signal of the operational amplifier and generates a signal when the amplifier output signal exceeds a threshold value.

3. A monitor as claimed in claim 2, wherein the detector detects when the amplifier output signal is saturated.

4. A monitor as claimed in claim 1, wherein the circuit that adjusts the current at the working sensor terminal when the current between the terminals exceeds the predetermined threshold comprises a field effect transistor connected between the terminals of the sensor, the circuit reducing the resistance of the transistor when the detector detects an excessive current, thereby allowing current to flow between the sensor terminals.

5. A monitor as claimed in claim 1, wherein the circuit that adjusts the current at the working sensor terminal when the current between the terminals exceeds the predetermined threshold comprises a current source and a transistor to connect the current source to the working electrode, thereby reducing the potential difference between the sensor terminals.

6. A monitor as claimed in claim 1, wherein the circuit that adjusts the current at the working sensor terminal when the current between the terminals exceeds the predetermined threshold comprises a current drain and a switch, an a transistor to connect the current drain to the working electrode, thereby reducing the potential difference across the sensor terminals.

7. A monitor as claimed in claim 1, which includes a 2-terminal electrochemical gas sensor connected to the terminals.

8. A method of monitoring an atmosphere for the presence of a target gas by means of a 2-terminal electrochemical gas sensor having a working (sensing) electrode and a counter electrode, the sensor providing a current between the electrodes that is indicative of the amount of target gas in the atmosphere, the method comprising:
   a) detecting when the current flowing between the sensor terminals exceeds a predetermined threshold associated with saturation of an amplifier driven by the current flowing between the sensor terminals; and
   b) restricting the potential difference between the sensor terminals with a transistor, a source and a drain of the transistor connected to the working and counter electrodes of the sensor, respectively, when the current between the terminals exceeds the predetermined threshold by supplying additional current to or removing current from the working sensor terminal in order to oxidize substantially all of the target gas in contact with the working electrode until the amplifier is no longer saturated.

9. A method of monitoring an atmosphere for the presence of a target gas by means of a 2-terminal electrochemical gas sensor having a working (sensing) electrode and a counter electrode, the sensor providing a current between the electrodes that is indicative of the amount of target gas in the atmosphere, the method comprising:
   a) detecting when the current flowing between the sensor terminals exceeds a predetermined threshold associated with saturation of an amplifier driven by the current flowing between the sensor terminals; and
   b) restricting the potential difference between the sensor terminals with a circuit connected across the working and counter electrodes of the sensor when the current between the terminals exceeds the predetermined threshold by supplying additional current to or removing current from the working sensor terminal in order to oxidize substantially all of the target gas in contact with the working electrode until the amplifier is no longer saturated wherein additional current is supplied to or current is removed from the working sensor terminal in step b) by connecting and directing current through a variable resistance bypass circuit in parallel to the working and the counter electrodes and reducing the resistance of the bypass circuit so that current flows between the working and the counter electrodes.

10. A method as claimed in claim 8, wherein additional current is supplied to the working sensor terminal in step b) by injecting current from a current source.

11. A method as claimed in claim 8, wherein current is removed from the working sensor terminal in step b) via a current drain.

12. A monitor for use with a 2-terminal sensor for monitoring an atmosphere for the presence of a target gas, the monitor comprising:
   a) two terminals for connection, respectively, to a working (sensing) electrode and a counter electrode of an electrochemical gas sensor, the sensor providing a current between the terminals that is indicative of the amount of target gas in the atmosphere, said monitor having only two contacts for connection to the sensor;
   b) an operational amplifier, an inverting input of the operational amplifier coupled to the working (sensing) electrode of the electrochemical gas sensor via a first pathway and a non-inverting input of the operational amplifier coupled to ground to generate an output signal according to the current flowing between the terminals, whereby the output signal is indicative of the amount of target gas in the atmosphere;
   c) a detector for detecting when the current flowing between the sensor terminals exceeds a predetermined threshold associated with saturation of the operational amplifier, the detector includes a feedback circuit having an analog-to-digital converter coupled to the output signal, a digital processor coupled to the converter and a digital-to-analog converter which produces an analog feedback signal; and
   d) a circuit that restricts the potential difference between the sensor electrode terminals by detecting that the current between the terminals exceeds the predetermined threshold and by injecting additional current to or removing current from the working sensor terminal via the first pathway, the circuit is coupled to the feedback signal, and where the feedback circuit controls the injection or removal of current from the working sensor by the circuit in order to oxidize substantially all of the target gas in contact with the working electrode until the operational amplifier is no longer saturated.

13. A monitor as claimed in claim 12 wherein the circuit that adjusts the current at the working sensor terminal when the current between the terminals exceeds the predetermined threshold comprises a variable resistance device, a field effect transistor, connected between the terminals of the sensor, the circuit reducing the resistance of the transistor when the detector detects an excessive current, thereby allowing current to flow between the sensor terminals.

14. A monitor as claimed in claim 12 wherein the circuit that adjusts the current at the working sensor terminal when the current between the terminal exceeds the predetermined threshold comprises a current source and a switch to connect the current source to the working electrode, thereby reducing the potential difference between the sensor terminals.

15. A monitor as claimed in claim 14 wherein the switch is a transistor.

16. A monitor as claimed in claim 12 wherein the circuit that adjusts the current at the working sensor terminal when the current between the terminals exceeds the predetermined threshold comprises a current drain and a switch to connect the current drain to the working electrode, thereby reducing the potential difference across the sensor terminals.

17. A monitor as claimed in claim 16 wherein the switch is a transistor.

18. A monitor as claimed in claim 12 wherein the digital processor monitors the output signal and the digital processor generates a signal to reduce a resistance of the circuit when the output signal reaches the predetermined threshold.

19. A monitor as claimed in claim 12 wherein the digital processor monitors the output signal and the digital processor generates a signal to inject a current into the circuit when the output signal reaches the predetermined threshold.

* * * * *